United States Patent [19]

Rhodes et al.

[11] Patent Number: 5,104,802
[45] Date of Patent: Apr. 14, 1992

[54] HOLLOW FIBER CLINOSTAT FOR SIMULATING MICROGRAVITY IN CELL CULTURE

[75] Inventors: Percy H. Rhodes, Huntsville; Teresa Y. Miller, Falkville; Robert S. Snyder, Huntsville, all of Ala.

[73] Assignee: The United States of America as represented by the Administrator of the National Aeronautics and Space Administration, Washington, D.C.

[21] Appl. No.: 386,175

[22] Filed: Jul. 28, 1989

[51] Int. Cl.⁵ .................... C12M 3/02; C12M 3/00; C12M 1/12; C12M 1/10
[52] U.S. Cl. .................... 435/286; 435/311; 435/312
[58] Field of Search .................... 435/284–287, 435/311, 312, 313; 422/72, 209, 101

[56] References Cited

U.S. PATENT DOCUMENTS

| | | | |
|---|---|---|---|
| 2,686,754 | 8/1954 | Monod | 435/313 |
| 3,394,880 | 7/1968 | Carter | 422/72 |
| 4,828,716 | 5/1989 | McEwen et al. | 422/72 |
| 4,876,013 | 10/1989 | Shmidt et al. | 422/101 |
| 4,939,087 | 7/1990 | Van Wie et al. | 435/286 |
| 4,988,623 | 1/1991 | Schwarz et al. | 435/284 |

FOREIGN PATENT DOCUMENTS

| | | | |
|---|---|---|---|
| 0112154 | 6/1984 | European Pat. Off. | |
| 0160229 | 5/1983 | Fed. Rep. of Germany | 435/312 |

OTHER PUBLICATIONS

Robertson, C. and Kim, I. H., Biotechnol. Bioeng. XXVII pp. 1012–1020 (1985).

Primary Examiner—David L. Lacey
Assistant Examiner—Jan M. Ludlow
Attorney, Agent, or Firm—Robert L. Broad, Jr.; Jerry L. Seemann

[57] ABSTRACT

A clinostat for simulating microgravity on cell systems carried in a fiber fixedly mounted in a rotatable culture vessel. The clinostat is rotated horizontally along its longitudinal axis to simulate microgravity or vertically as a control response. Cells are injected into the fiber and the ends of the fiber are sealed and secured to spaced end pieces of a fiber holder assembly which consists of the end pieces, a hollow fiber, a culture vessel and a tension spring with three alignment pins. The tension spring is positioned around the culture vessel with its ends abutting the end pieces and the alignment pins extend between the end pieces for alignment of the spring. After the fiber is secured, the spring is decompressed to maintain tension on the fiber while it is being rotated. This assures that the fiber remains aligned along the axis of rotation. The fiber assembly is placed in the culture vessel and culture medium is added. The culture vessel is then inserted into the rotatable portion of the clinostat and subjected to rotate at selected rpms. The internal diameter of the hollow fiber determines the distance the cells are from the axis of rotation.

5 Claims, 2 Drawing Sheets

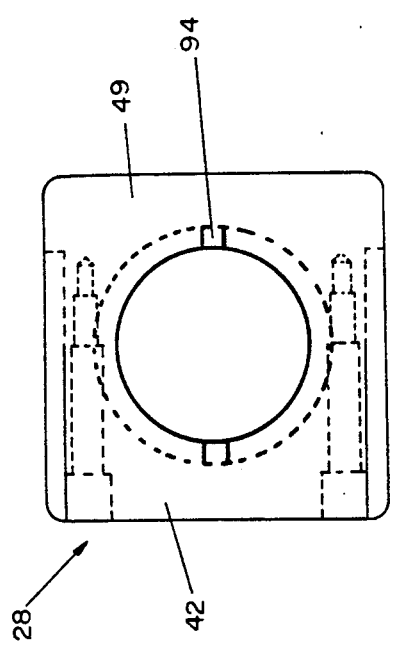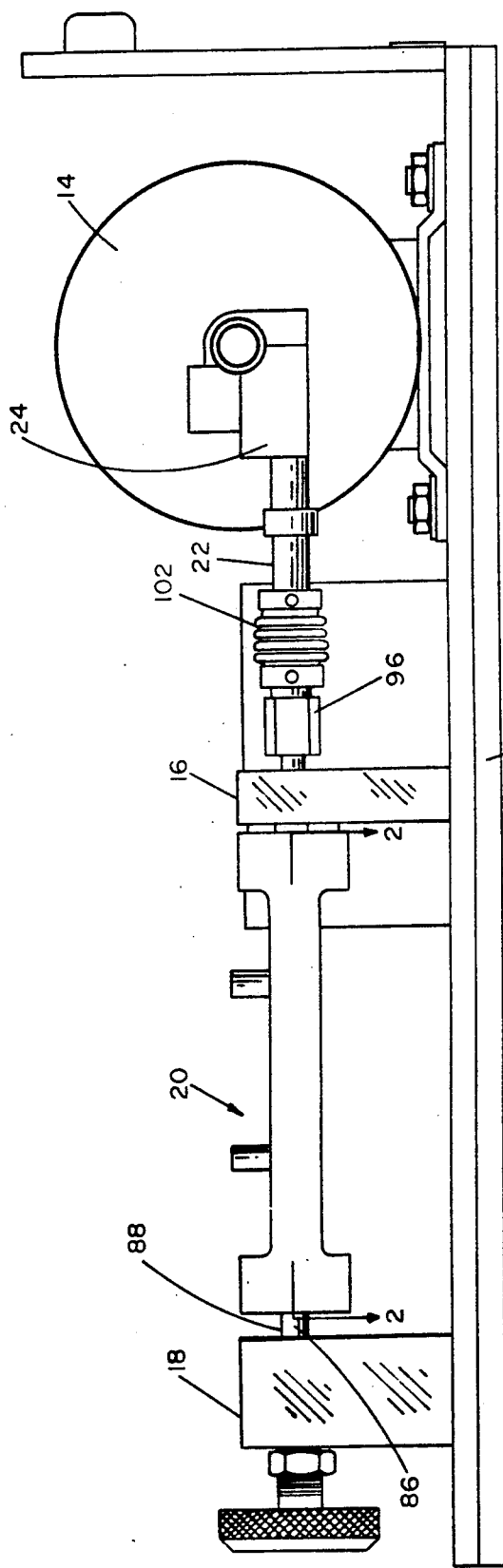

HOLLOW FIBER CLINOSTAT FOR SIMULATING MICROGRAVITY IN CELL CULTURE

ORIGIN OF THE INVENTION

The invention described herein was made by an employee of the United States Government and may be manufactured and used by or for the Government for governmental purposes without the payment of any royalties thereon or therefor.

FIELD OF THE INVENTION

This invention relates to apparatus for simulating microgravity on cell systems and more particularly to a rotating device for simulating microgravity on anchorage dependent cell systems.

BACKGROUND OF THE INVENTION

There are many prior art devices and methods for the cultivation of cells. Some such devices and methods provide for the free suspension of cells or organisms in the culture mediums (this is unacceptable for anchorage dependent samples), agar overlays (environment is not suitable for some types of cells or organisms), impalement (harmful to organisms studied) and growth on microscope coverslips or slides (less of the sample is contained near the axis of rotation).

There are various patents which relate to the cultivation of biology cells. U.S. Pat. No. 3,997,396, for example, discloses the general concept of attaching and growing cells on one side or surface of a hollow fiber membrane. U.S. Pat. Nos. 2,686,754, 3,540,700 and 3,732,149 generally disclose rotating apparatus for cell growth. U.S. Pat. No. 4,704,258 discloses apparatus for growth of crystal material in space, and, U.S. Pat. No. 4,184,922 discloses an artificial capillary bundle for cell culture.

U.S. Pat. No. 4,144,136 discloses an apparatus for cellular structure wherein a suspension of anchorage cells is introduced into a culture vessel containing a plurality of hollow tubes, and the culture vessel is rotated in such a manner and at a speed effective to cause adhesion of the cells on the inner walls of the culture vessel, and on the inner and outer walls of the tubes.

None of the above discloses the use of a hollow fiber having test organisms, including mammalian cells therein, which is supported in a culture vessel mounted in a rotating clinostat having tensioning means to maintain the fiber along the axis of rotation during rotation of the clinostat. The device simulates a microgravity within the test fiber.

It is an object of the present invention, therefore, to provide a ground based apparatus for simulating microgravity on cell systems.

It is another object of the present invention to provide such apparatus with rotation means for simulating the microgravity environment.

It is a further object of the present invention to provide such apparatus with a culture chamber for support of a cell containing fiber therein, the fiber being mounted for rotation with the culture chamber.

It is yet another object of the present invention to provide such an apparatus with tensioning means for applying a predetermined tensile force on said fiber for maintaining the fiber in alignment with the axis of rotation of the vessel.

It is still yet another object of the present invention to provide such apparatus with alignment means for maintaining the tensioning means in alignment along the axis of rotation of the rotation means.

BRIEF DESCRIPTION OF THE DRAWINGS

FIG. 1 is an elevational view of the apparatus for simulating microgravity on cell systems.

FIG. 4 is an end elevational view along line 4—4 of FIG. 2.

DESCRIPTION OF THE PREFERRED EMBODIMENT

Figure 2:
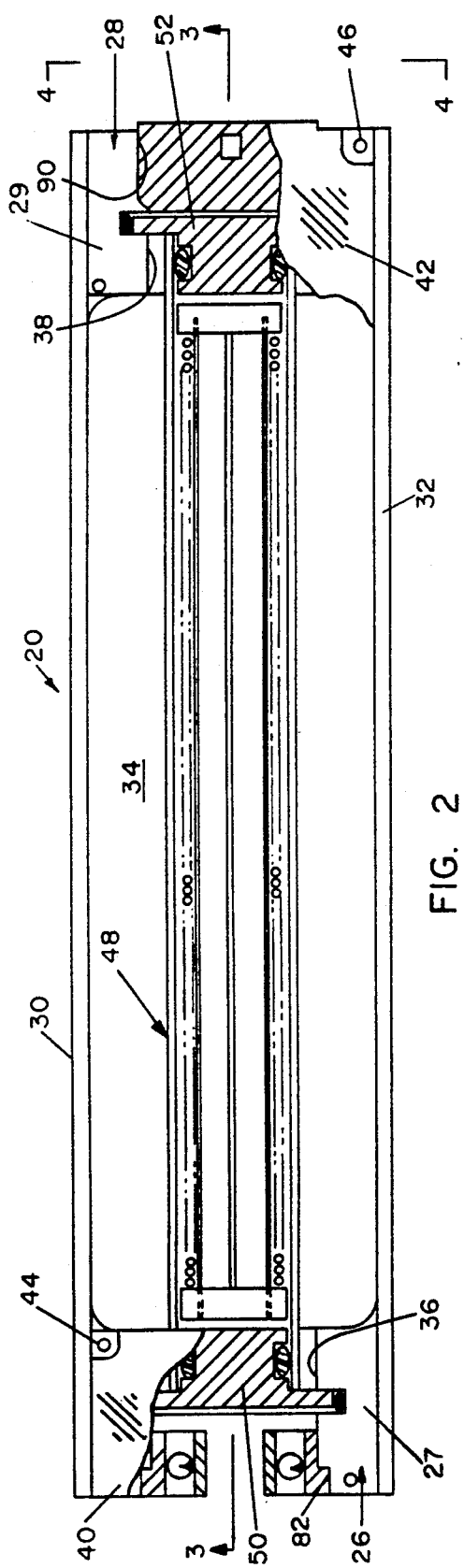
FIG. 2 is a sectional view of the cell system support structure taken along line 2—2 of FIG. 1.

As seen in FIG. 1, a clinostat assembly 10 is shown to include a horizontal base plate 12 having thereon an electric motor 14, a forward support 16 and a rear support 18. An elongated culture vessel support assembly 20 is disposed between forward and rear supports 16 and 18. Culture vessel support assembly 20 is adapted to rotate on its elongated axis by rotation of a drive shaft 22 which is geared by a transmission 24 to the output shaft of motor 14.

Figure 3:
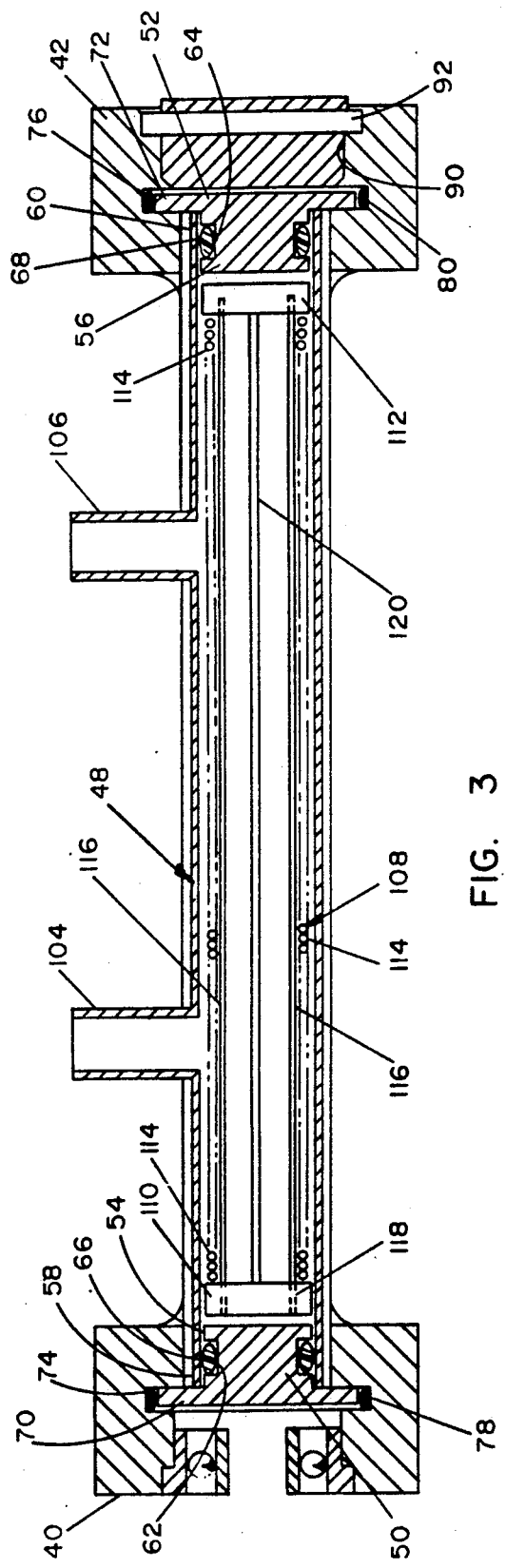
FIG. 3 is a sectional view of the cell system support structure as seen along line 3—3 of FIG. 2.

The culture vessel support assembly 20 is provided with a pair of spaced end assemblies 26 and 28 (FIGS. 2 and 3) each including an end support member 27 and 29, respectively. A pair of spaced side members 30 and 32 is made integral with end support members 27 and 29 and extend therebetween defining an elongated space 34. Each end member 27 and 29 is provided with a cylindrical passageway 36 and 38 respectively extending along their elongated axis and each end assembly includes a removable cap 40 and 42 (FIGS. 2 and 4), respectively, held in place by pairs of bolts 44 and 46 which are screwed into their respective end support members 27 and 29. A cylindrical glass tube (culture vessel) 48 extends between end assemblies 26 and 28 and is supported at its ends in each end assembly 26 and 28 by cylindrical closure members 50 and 52, respectively, (FIGS. 2 and 3). Closure members 50 and 52 are respectively provided with a reduced diameter portion 54 and 56 which extends partially into the opposite ends 58 and 60 of glass tube 48. The external diameter of portions 54 and 56 substantially matches the internal diameter of the glass tube. The closure members are respectively provided, in reduced portions 54 and 56 thereof, with a circumferential groove 62 and 64, respectively, which retains elastomeric rings 66 and 68 therein. Each of the closure members 50 and 52 further includes a flanged end 70 and 72 which respectively seat in a circumferential groove 74 and 76 provided in end assemblies 26 and 28. O-ring seals 78 and 80 are disposed in grooves 74 and 76.

End assembly 26 includes an axial passageway 82 having a ball bearing race 84 fitted therein which receives the journaled end 86 (FIG. 1) of an adjustable shaft 88 that is threaded into the rear upstanding support 18 (FIG. 1). End assembly 28 (FIGS. 2 and 3) includes an axial passageway 90 having a recess 92 provided with key slots 94 that receives a drive member 96 (FIG. 1) on the end of drive shaft 22 (FIG. 1). Drive member 96 includes an extending portion 98 which extends through bearing races (not shown) in the front upstanding support 16. The drive shaft 22 is provided with a flexible coupling 102 (FIG. 1) that connects to the drive member 96. The transmission gears (not shown) are powered by a rotating shaft of the motor 14. Thus it can be seen that rotation of the drive shaft 22 causes rotation of the culture vessel assembly 20 through the action of the key members extending from the drive member 96.

Tube 48 includes (FIG. 3) a pair of spaced upstanding tubular members 104 and 106 which form entry ports to the tube body. Within the elongated tube body 48 is a fiber support assembly 108 having two end pieces 110 and 112 with a coil spring 114 extending therebetween. Three spaced guide pins 116 (only two shown) also extend between the two end pieces to keep the spring assembly in proper alignment. The guide pins 116 are fixed to one of the end pieces illustrated as 112 but extend through holes 118 within the other end piece illustrated as 110 permitting it to slide along the guide pins. A hollow fiber 120 is secured to and extends between the end pieces 110 and 112 of fiber support assembly 108 so as to be rotated along the axis of the culture vessel.

The hollow fiber 120 serves to hold the biological cells which are usually injected into the lumen of the fiber with the spring compressed, after which the ends of the fiber are sealed with wax or heat alone and positioned between the two end pieces. The fiber 120 is secured to the end pieces 110 and 112 with wax or glue, after which the coil spring 114 is decompressed so as to force the two end pieces apart. This assures that the fiber 120 remains aligned along the axis of rotation should some stretching of the fiber occur during rotation. The fiber 120 is a standard commercial type normally used in groups for cell culture. The fiber 120 with the end pieces 110 and 112 are placed into the glass tube 48 which serves as the culture vessel.

The fiber 120 is permeable to the culture media which is inserted into the glass tube 48 through the ports 104 and 106 after which the ports are sealed with a silicon cap. The glass tube 48 is then placed into the rear and front end members 26 and 28 and clamped down by the bolting down of the caps 40 and 42.

When the fiber assembly is in place, the motor 14 is turned on to rotate the assembly about its elongated axis at a selected rpm in either the vertical or horizontal position. The ports 104 and 106 of the glass tube 48 provide access to the culture media for media exchange, media sampling or the injection of various biochemical agents for specific experimental protocols or for fixation.

The internal diameter of the hollow fiber 120, which is a standard commercial type, determines the distance the cells are from the distance of axis of rotation of the chamber. Different diameter fibers can be selected at the discretion of the experimenter.

The clinostat described is effective in generating sufficient centrifugal force to counteract the gravity vector by rotating the fiber along its axis thus effectively simulating microgravity.

It is thus apparent that a novel rotating fiber clinostat has been made which contains the cell sample near the axis of rotation.. The assembly is easy to operate and provides ease of aseptic assembly and sampling handling both for experiment initiation and analysis.

An example of the use of the clinostat is as follows. Thigh muscle from a 12 day broiler chick embryos is removed and disaggregated into individual cells by vortexing the muscle in growth medium on a vortex mixer at a maximum speed for 2030 seconds. The suspension is filtered through nylon mesh to remove connective tissue and bone. The cells are recovered by centrifugation. Following resuspension in an appropriate amount of growth medium (Eagle's Minimum Essential Medium containing 5% chick extract, 10% horse serum, 50 units/ml penicillin, 50 µg/ml streptomycin, 2.5 µg/ml fungizone) to give a concentration of $1.5 \times 10$ cells/ml. The cell suspension is injected into a 70 mm long piece of 0.5 mm (inner diameter) XM-80 hollow fiber 120 using a 1cc syringe and a $26\frac{3}{8}$ gauge needle. Both ends of the fiber are sealed with hot wax and the fiber is loaded into the glass tube containing 5 ml of complete media. The glass tube is sealed and the entire assembly is loaded into the clinostat.

The clinostat disclosed permits a wide range of microgravity simulation studies including: suspension cultures of cells or organisms by selecting rotations which maintain the position of the cells within the internal dimensions of the fiber; larger quantities of the cells can be tested by lenghtening the hollow fiber, and hollow fiber support assembly which includes the culture vessel. Slip type connectors and tubing can be added for continual circulation of culture media through the culture vessel allowing constant monitoring of various parameters such as pH, conductivity, and oxygen and carbon dioxide, as well as, other biochemical substances of interest and providing a method for varying the concentration of substances contained within the culture media. Anchorage dependent cells types or organisms could also be grown on beads which in turn are injected into the hollow fiber. This could facilitate removal of cell samples from the fiber.

I claim:

1. A ground based apparatus for simulating microgravity on biology cell systems comprising
   a. support means,
   b. an elongated culture vessel rotably mounted on the support means, said support means including an end support assembly positioned at each end of the culture vessel,
   c. an elongated tubular porous fiber mounted in the culture vessel and having closed ends for holding biological cells,
   d. means for rotating one of the end support assemblies to rotate the culture vessel and said tubular porous fiber about an axis of rotation, said axis of roation and the longitudinal axis of the tubular fiber being the same, and
   e. an elongated spring surrounding the fiber, wherein the ends of said spring are in abutment with the end assemblies to apply a tension to the fiber.

2. Apparatus as set forth in claim 1 including alignment means comprising a plurality of spaced rods, said rods being rigidly affixed to one of said end assemblies and slideable in a second of said end assemblies.

3. Apparatus as set forth in claim 2 wherein each said end assembly includes an end culture vessel support member and a removable plate secured to each of said end culture vessel support members to permit insertion and removal of said culture vessel from said end assemblies.

4. Apparatus as set forth in claim 3 wherein said means for rotating is a motor having an output shaft, said output shaft connected to a first of said end assemblies for rotation of said tubular porous fiber responsive to energization of said motor.

5. Apparatus as set forth in claim 4 wherein said support means comprises a base member having a pair of spaced upstanding support members thereon, a first of said upstanding support members disposed for supporting said motor output shaft and said first end assembly, said second upstanding support means disposed for supporting the second of said end assemblies.

* * * * *